(12) United States Patent  (10) Patent No.: US 6,318,860 B1
Suzumura  (45) Date of Patent: Nov. 20, 2001

(54) PERIMETER

(75) Inventor: Yoshikatsu Suzumura, Hamamatsu (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 09/507,198

(22) Filed: Feb. 18, 2000

(30) Foreign Application Priority Data

Mar. 19, 1999 (JP) .................................................. 11-074733

(51) Int. Cl.⁷ ........................................................ A61B 3/14
(52) U.S. Cl. .............................................................. 351/224
(58) Field of Search ..................................... 351/200, 201, 351/203, 224, 225, 226, 205, 206, 210

(56) References Cited

U.S. PATENT DOCUMENTS 4,279,478 * 7/1981 Matsumura ........................... 351/206
5,094,522 * 3/1992 Sourdille et al. ..................... 351/210

* cited by examiner

Primary Examiner—George Manuel
(74) Attorney, Agent, or Firm—Adams & Wilks

(57) ABSTRACT

A perimeter has an image input for inputting eye fundus image data and a display device for displaying an eye fundus image in accordance with the eye fundus image data inputted by the image input. A prescribed area of the eye fundus image displayed on the display device is designated by a designating device. A field of vision of only the prescribed area of the eye fundus image designated by the designating device is then measured by a measurement device.

10 Claims, 2 Drawing Sheets

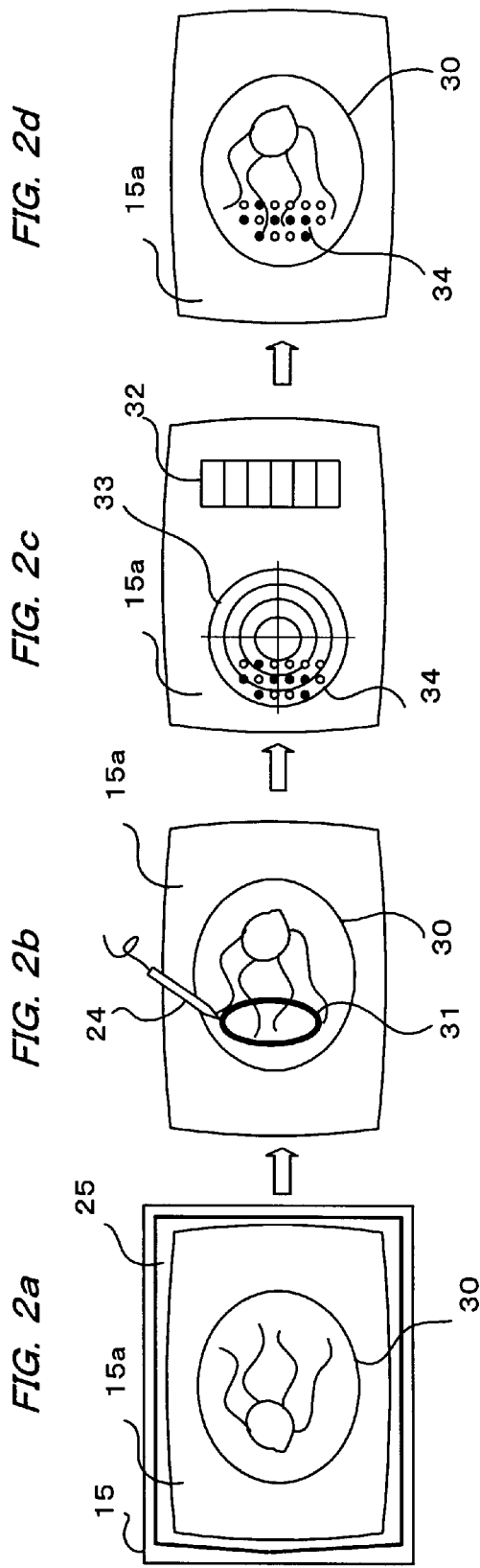

PERIMETER

BACKGROUND OF THE INVENTION

1. Field of the Invention

This invention relates to a perimeter, and more particularly to a perimeter that enables a field of vision measurement area to be designated from an eye fundus image.

2. Description of the Prior Art

Perimetry has long had a widely-recognized utility with respect to ailments in the eye fundus. Measurement comprises establishing whether or not the patient can perceive a visual sign displayed at a prescribed brightness within a prescribed field of vision (field of vision dome). There is a relationship between the field of vision and ailments in the eye fundus, so when the eye fundus is being examined by measuring the field of vision, the examiner proceeds by viewing a photograph of the patient's eye fundus, designating a measurement area on another screen, and measuring the field of vision accordingly.

A drawback of the conventional method is that since the examiner has to view a photograph of the eye fundus and then use another screen to designate the measurement area of the field of vision, the area designation is imprecise and efficiency is degraded during the designation.

In recent years, when a fundus camera is used to examine the eye fundus, images of the fundus are recorded on film, or the images are obtained using a video imaging means such as a CCD camera, converted into an electronic form and stored on floppy disk or other such external storage means, or is transferred to another computer via a LAN or the like.

SUMMARY OF THE INVENTION

An object of the present invention is to provide a perimeter that is able to detect field of vision abnormalities accurately and efficiently.

In accordance with this invention, the above object is attained by providing a perimeter comprising means for inputting eye fundus electronic image data, display means for displaying the eye fundus image data thus input, means for designating a prescribed area of the eye fundus image displayed on the display means, and a measurement program for carrying out field of vision measurement of the area thus designated.

BRIEF DESCRIPTION OF THE DRAWINGS

These and other objects and advantages of the invention will be more apparent from the following description and drawings, in which:

FIGS. 2a to 2d are a diagram illustrating the process of measuring the field of vision.

DESCRIPTION OF THE PREFERRED EMBODIMENT

Figure 1:
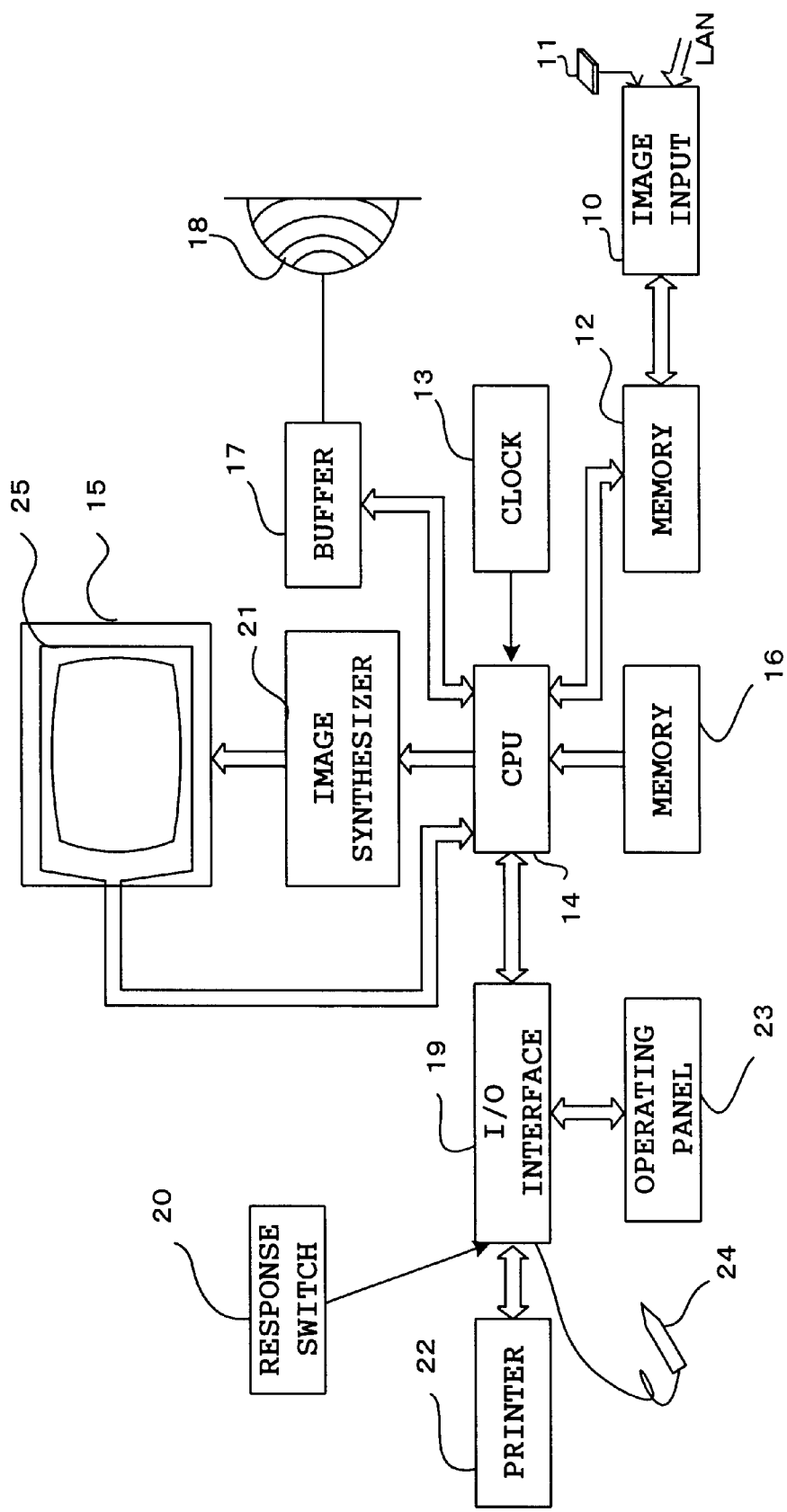
FIG. 1 is a block diagram of the general arrangement of a perimeter according to the present invention.

Embodiments of the invention will now be described with reference to the attached drawings.

In FIG. 1, reference numeral 10 denotes an image input section. Eye fundus electronic image data are input to the image input section 10 from a removable disk such as a floppy disk 11, or from a LAN or the like. An eye fundus video camera (not shown), such as a CCD camera, is used to obtain eye fundus images, which are then processed and stored on a floppy disk 11 or the like, or are received via a LAN or the like. The eye fundus images input to the image input section 10 are first stored in a memory 12, and, via a CPU 14 operating in synchronism with a clock 13, the images can be displayed on a display such as a monitor 15.

A field of vision measurement program is stored in a memory 16. When, as will be described later, a prescribed area of the eye fundus displayed on the monitor 15 is designated, the CPU 14 initiates to display a series of visual indicators, via a buffer 17, on a field of vision dome 18. The display of these visual indicators may be effected by projecting the indicators on the field of vision dome or by lighting a light source such as an LED or the like provided on the field of vision dome. The indicators are displayed on the field of vision dome in association with the designated area of the eye fundus, so that the visual indicators thus displayed form an image at the designated area of the eye fundus, assuming that the patients vision is fixed on the center of the field of vision dome.

When the patient can see a visual indicator displayed on the field of vision dome 18, the patient responds with a response switch 20. This signal is transferred to the CPU 14 via an I/O interface 19. The CPU 14 can process the outcome of the field of vision measurement and display it on the monitor 15. Also, the CPU 14 is constructed so that it processes and synthesizes the images in cooperation with an image synthesizer 21 and the thus synthesized images can be displayed on the monitor 15.

The I/O interface 19 is connected to an operating panel 23 that is equipped with an LED or other such light source. This operating panel 23 can be used to implement the various operations such as image input, field of vision measurement, image synthesis and so forth. Operations thus initiated at the operating panel 23 are communicated to the CPU 14 via the I/O interface 19. The results of measurements and images displayed on the monitor 15 can be output to a printer 22 via the I/O interface 19. A light-pen 24 can be used to designate areas of images displayed on the monitor via the I/O interface 19. Instead of using the light-pen a touch-panel 25 provided on the monitor 15 can be used for this purpose.

In operation, eye fundus image data input to the image input section 10 via a floppy disk 11, a LAN or the like are once stored in the memory 12, and then, via the CPU 14, is displayed on the monitor 15. This is illustrated by FIG. 2a, showing eye fundus image 30 on monitor screen 15a. In FIGS. 2a to 2d, only the monitor screen 15a is shown; the monitor frame and touch-panel 25 are thus not shown.

Next, as shown in FIG. 2b, a prescribed area 31 of the eye fundus image is designated, using the light-pen 24 or a finger. The area is designated so as to include at least a portion considered to be, for example, a diseased portion of the eye fundus. The designation of the area 31 is communicated to the CPU 14, which executes the measurement program stored in the memory 16 to implement field of vision measurement of the designated portion. FIG. 2c shows this field of vision measurement on the monitor screen 15a; the contents of the measurement program thus implemented are shown in region 32, and the results 34 of the field of vision measurement implemented on the field of vision dome image 33 are displayed. The solid black dots in the result field each denote a non-response by the patient to a visual indicator that was displayed on the field of vision dome, indicating a field of vision abnormality.

The results 34 are stored in the memory 12 as field of vision measurement data. The image synthesizer 21 can take the result data and overlay them on the eye fundus data displayed on the screen 15a, as shown in FIG. 2d. The field of vision measurement data can also be associated with the eye fundus image data and stored in the memory 12 or in an external memory that is not shown. If required, displayed images can be printed out.

As described in the foregoing, this invention allows an area of an eye fundus that is to be subjected to field of vision measurement to be designated using a screen on which the fundus image is displayed, thereby enabling field of vision abnormalities to be detected with good efficiency.

What is claimed is:

1. A perimeter comprising:

input means for inputting eye fundus image data;

display means for displaying an eye fundus image in accordance with the eye fundus image data inputted by the input means;

designating means for designating a prescribed area of the eye fundus image displayed on the display means; and measurement means for measuring a field of vision of only the prescribed area of the eye fundus image designated by the designating means.

2. A perimeter according to claim 1; wherein the display means includes means for displaying results of the field of vision measured by the measurement means while simultaneously displaying the eye fundus image data.

3. A perimeter according to claim 2; further comprising printing means for printing images of the eye fundus and the results of the field of vision measurement displayed by the display means.

4. A perimeter according to claim 2; further comprising storage means for storing results of the field of vision measurement and the eye fundus image data.

5. A perimeter according to claim 1; wherein the prescribed area of the eye fundus image comprises a diseased portion of the eye fundus.

6. A perimeter comprising: input means for inputting eye fundus image data; display means for displaying an eye fundus image in accordance with the eye fundus image data inputted by the input means; designating means for designating a prescribed area of the eye fundus image displayed on the display means; means for displaying a plurality of visual indicators to form an image of the visual indicators at the prescribed area of the eye fundus image; and measurement means for measuring a field of vision of a plurality of points within the prescribed area of the eye fundus image designated by the designating means in accordance with detected responses by a patient upon visualization by the patient of the visual indicators displayed at the prescribed area of the fundus image.

7. A perimeter according to claim 6; wherein the prescribed area of the eye fundus image comprises a diseased portion of the eye fundus.

8. A perimeter according to claim 6; wherein the display means includes means for displaying results of the field of vision measured by the measurement means while simultaneously displaying the eye fundus image data.

9. A perimeter according to claim 8; further comprising printing means for printing images of the eye fundus and the results of the field of vision measurement displayed on the display means.

10. A perimeter according to claim 8; further comprising storage means for storing results of the field of vision measurement and the eye fundus image data.

* * * * *